United States Patent [19]

Kume et al.

[11] Patent Number: 4,971,619
[45] Date of Patent: Nov. 20, 1990

[54] BENZOTHIAZOLONE

[75] Inventors: Toyohiko Kume; Toshio Goto; Atsumi Kamochi; Akihiko Yanagi; Shigeki Yagi; Hiroshi Miyauchi, all of Tokyo, Japan

[73] Assignee: Nihon Tokushu Noyaku Seizo K.K., Tokyo, Japan

[21] Appl. No.: 378,729

[22] Filed: Jul. 12, 1989

[30] Foreign Application Priority Data

Jul. 21, 1988 [JP] Japan ............... 63-180419
Oct. 22, 1988 [JP] Japan ............... 63-266663

[51] Int. Cl.$^5$ .................... C07D 417/10; A01N 43/78
[52] U.S. Cl. ............................ 71/90; 548/171
[58] Field of Search ............... 548/171; 71/90

[56] References Cited

U.S. PATENT DOCUMENTS 4,720,297 1/1988 Hage ............................ 71/90

FOREIGN PATENT DOCUMENTS 68822 1/1983 European Pat. Off. ........... 548/546

*Primary Examiner*—Robert Gerstl
*Attorney, Agent, or Firm*—Sprung Horn Kramer & Woods

[57] ABSTRACT

Herbicidal benzothiazolones of the formula

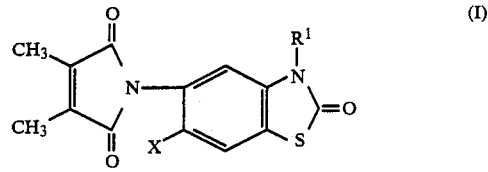

wherein X represents hydrogen or halogen,
$R^1$ represents hydrogen, alkyl, various organic radicals,

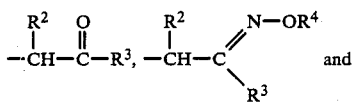

and

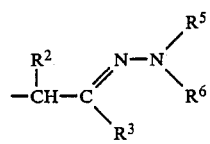

in which
$R_2$, $R^4$, $R^5$ and $R^6$ each is hydrogen or an organic radical, and $R^3$ is alkyl, cycloalkyl or optionally halo-substituted phenyl.

13 Claims, No Drawings

BENZOTHIAZOLONE

This application is a continuation-in-part of application Ser. No. 209,170 filed June 17, 1988, now U.S. Pat. No. 4,902,335 and of application Ser. No. 378,729, filed July 12, 1989, now allowed.

The present invention relates to novel benzothiazolones, to processes for their preparation and to their use as herbicides.

It has already been disclosed that certain 3,4-dimethylmaleinimides were used for an intermediate of herbicidally active 3,4-dimethyl-2-hydroxy-5-oxo-2,5-dihydropyrroles (see U.S. Pat. No. 4,138,243), and also that certain benzothiazolones had herbicidal function (see Japanese Patent Laid-open No. 155,276/1987).

There have now been found novel benzothiazolones of the following formula (I)

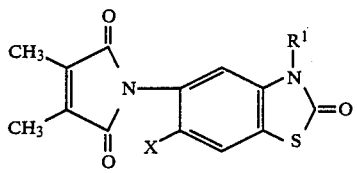
(I)

wherein X represents hydrogen or halogen,
$R^1$ represents hydrogen, alkyl with 1 to 5 carbon atoms optionally substituted with halogen, alkenyl with 3 to 5 carbon atoms optionally substituted with halogen, alkynyl with 3 to 4 carbon atoms optionally substituted with halogen, alkoxyalkyl with 2 to 5 carbon atoms in total, alkylthioalkyl with 2 to 5 carbon atoms in total, alkylsulfinylalkyl with 2 to 5 carbon atoms in total, alkylsulfonylalkyl with 2 to 5 carbon atoms in total; arylthioalkyl with 7 to 8 carbon atoms in total, preferably phenylthioalkyl with 1 or 2 carbon atoms in the alkyl part, and optionally substituted with halogen, cyanoalkyl having an alkyl moiety with 1 to 2 carbon atoms, carbamoylmethyl, thiocarbamoylmethyl, alkoxycarbonylalkyl with 3 to 8 carbon atoms in total, cycloalkoxycarbonylmethyl having a cycloalkyl moiety with 3 to 7 carbon atoms, trialkylsilylmethyl with 4 to 10 carbon atoms in total, or a radical having any of the following formulae:

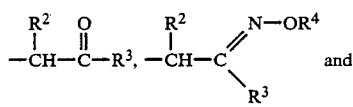 and

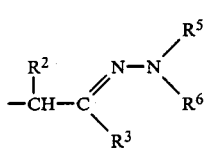

in which
$R^2$ represents hydrogen or alkyl with 1 to 3 carbon atoms,
$R^3$ represents alkyl with 1 to 4 carbon atoms, cycloalkyl with 3 to 6 carbon atoms, or phenyl optionally substituted with halogen,
$R^4$ represents hydrogen, alkyl with 1 to 4 carbon atoms, alkenyl with 3 to 4 carbon atoms, alkynyl with 3 to 4 carbon atoms, aralkyl with 7 to 9 carbon atoms in total, preferably phenylalkyl with 1 to 3 carbon atoms in the alkyl part, alkylcarbonyl having an alkyl moiety with 1 to 4 carbon atoms, or alkanesulfonyl with 1 to 4 carbon atoms, and
$R^5$ and $R^6$ each represent hydrogen or alkyl with 1 to 4 carbon atoms.

Benzothiazolones of the formulae (I) are obtained when (a) compounds of the formula (Ia)

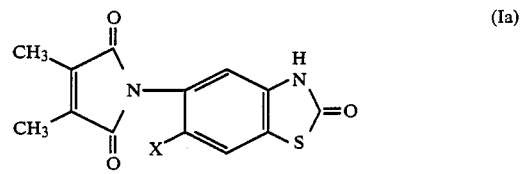
(Ia)

wherein X has the same meaning as stated above, are reacted with compounds of the formula (III)

(III)

wherein $R^1$ has the same meaning as stated above, and $M^1$ is halogen, in the presence of inert solvents, and if appropriate in the presence of bases, or (b) compounds of the formula (IV)

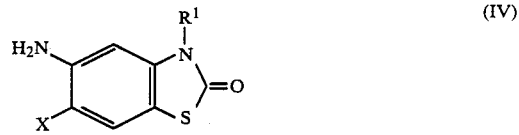
(IV)

wherein X and $R^1$ have the same meanings as stated above, are reacted with 2,3-dimethylmaleic anhydride in the presence of inert solvents, or (c) in the case where $R^1$ is alkylsulfinylalkyl with 2 to 5 carbon atoms in total or alkylsulfonylalkyl with 2 to 5 carbon atoms in total, compounds of the formula (Ib)

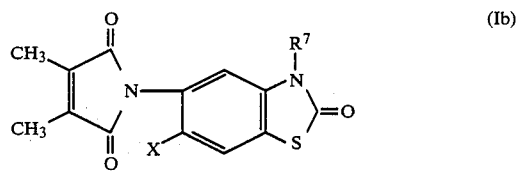
(Ib)

wherein X has the same meaning as stated above, and $R^7$ is alkylthioalkyl with 2 to 5 carbon atoms in total, are oxidized in the presence of inert solvents, or (d) in the case where $R^1$ is

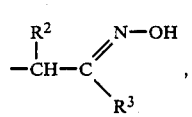

compounds of the formula (Ic)

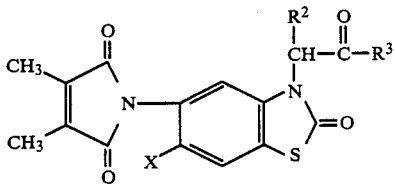

wherein X, R² and R³ have the same meanings as stated above, are reacted with hydroxylamine in the presence of inert solvents, or (e) in the case where R¹ is

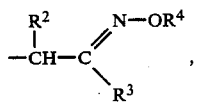

compounds of the formula (Id)

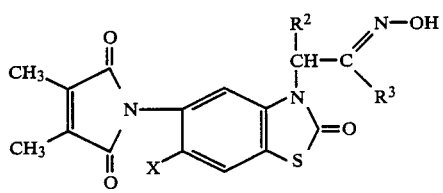

wherein X, R² and R³ have the same meanings as stated above, are reacted with compounds of the formula (VII)

$$M^1-R^4 \quad (VII)$$

wherein R⁴ and M¹ have the same meanings as stated above, in the presence of inert solvents, and if appropriate in the presence of bases.

The novel benzothiazolones exhibit powerful herbicidal properties.

Surprisingly, the benzothiazolones according to the invention, specifically shown in the working examples hereinafter, exhibit a substantially greater herbicidal function than those from the prior art cited hereinbefore. Optional substitution with halogen means that the radical may be mono- or polysubstituted identically or differently by fluorine, chlorine, bromine or iodine, preferably by fluorine or chlorine, in particular by chlorine. Optional substitution with chlorine means that the radical may be mono or polysubstituted, preferably up to pentasubstituted, in particular up to trisubstituted, by chlorine. Among the benzothiazolones according to the invention, of the formula (I), preferred compounds are those in which X represents hydrogen or fluorine, R¹ represents hydrogen, alkyl with 1 to 4 carbon atoms optionally substituted with chlorine, alkenyl with 3 to 4 carbon atoms optionally substituted with chlorine, alkynyl with 3 to 4 carbon atoms optionally substituted with chlorine, alkoxyalkyl with 2 to 4 carbon atoms in total, alkylthioalkyl with 2 to 3 carbon atoms in total, alkylsulfinylalkyl with 2 to 4 carbon atoms in total, alkylsulfonylalkyl with 2 to 4 carbon atoms in total, phenylthiomethyl optionally substituted with chlorine in the phenyl part, cyanomethyl, carbamoylmethyl, thiocarbamoylmethyl, alkoxycarbonylalkyl with 3 to 6 carbon atoms in total, cycloalkoxycarbonylmethyl having a cycloalkyl moiety with 3 to 6 carbon atoms, trimethylsilylmethyl, or a radical having any of the following formulas:

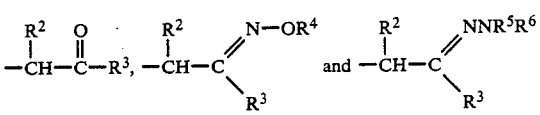

R² represents hydrogen, methyl or ethyl,

R³ represents alkyl with 1 to 3 carbon atoms, cycloalkyl with 3 to 5 carbon atoms, or phenyl optionally substituted with fluorine and/or with chlorine, R⁴ represents hydrogen, alkyl with 1 to 3 carbon atoms, allyl, propargyl, benzyl, alkylcarbonyl having an alkyl moiety with 1 to 3 carbon atoms, or alkanesulfonyl with 1 or 2 carbon atoms; and R⁵ and R⁶ each represents hydrogen or alkyl with 1 or 2 carbon atoms.

Very particularly preferred benzothiazolones of the formula (I) are those in which X represents fluorine.

R¹ represents hydrogen, alkyl with 1 to 3 carbon atoms optionally substituted with chlorine, allyl optionally substituted with chlorine, propargyl, alkoxymethyl having an alkoxy moiety with 1 to 3 carbon atoms, alkylthiomethyl having an alkylmercapto moiety with 1 or 2 carbon atoms, alkylsulfinylmethyl having an alkylsulfinyl moiety with 1 or 2 carbon atoms, alkylsulfonylmethyl having an alkylsulfonyl moiety with 1 or 2 carbon atoms, cyanomethyl, or a radical of the formula,

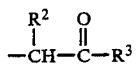

R² represents hydrogen or methyl, and

R³ represents methyl or ethyl.

Specifically, the following compounds may be mentioned;

5-(3,4-dimethylmaleinimido)-6-fluoro-3-propargyl-2-benzothiazolone, 3-allyl-5-(3,4-dimethylmaleinimido)-6-fluoro-2-benzothiazolone, 5-(3,4-dimethylmaleinimido)-6-fluoro-3-propyl-2-benzothiazolone, 3-cyanomethyl-5-(3,4-dimethylmaleinimido)-6-fluoro-2-benzothiazolone, 5-(3,4-dimethylmaleinimido)-6-fluoro-3-methylthiomethyl-2-benzothiazolone, 5-(3,4-dimethylmaleinimido)-6-fluoro-3-methylsulfinylmethyl-2-benzothiazolone, and 5-(3,4-dimethylmaleinimido)-6-fluoro-3-methylsulfonylmethyl-2-benzothiazolone.

If the starting materials employed in the process (a) are for instance, 5-(3,4-dimethylmaleinimido)-6-fluoro-2-benzothiazolone and propargyl bromide, the reaction may be illustrated by the following scheme:

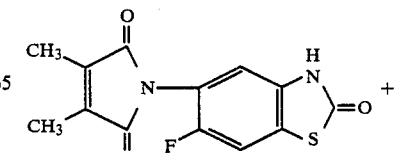

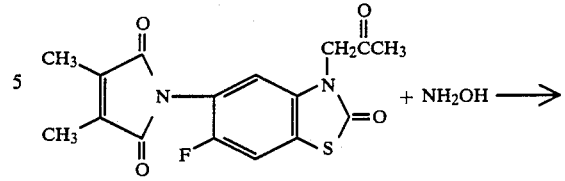

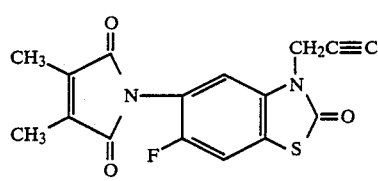

If the starting materials employed in the process (b) are, for instance, 5-amino-6-fluoro-3-propargyl-2-benzothiazolone and 2,3-dimethylmaleic anhydride, the reaction may be illustrated by the following scheme:

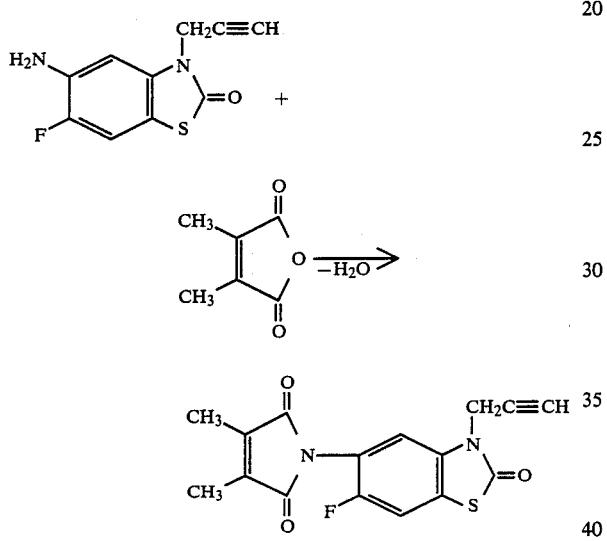

If the starting material employed in the process (c) is, for example, 5-(3,4-dimethylmaleinimido)-6-fluoro-3-methylthiomethyl-2-benzothiazolone, the oxidizing reaction may be illustrated by the following scheme:

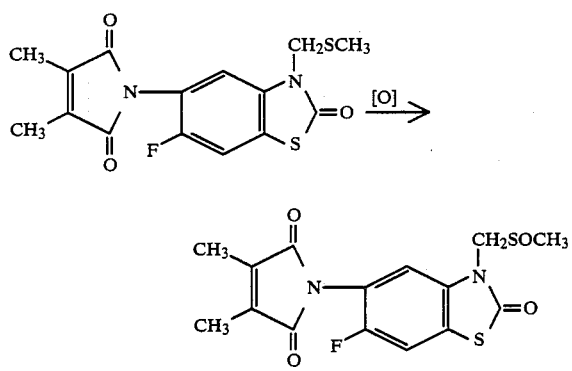

If the starting materials employed in the process (d) are, for instance, 5-(3,4-dimethylmaleinimido)-6-fluoro-3-(2-oxopropyl)-2-benzothiazolone and hydroxylamine, the reaction may be illustrated by the following scheme:

If the starting materials employed in the process (e) are, for instance, 5-(3,4-dimethylmaleinimido)-6-fluoro-3-(2-hydroxyimino-propyl)-2-benzothiazolone and iodomethane, the reaction may be illustrated by the following scheme:

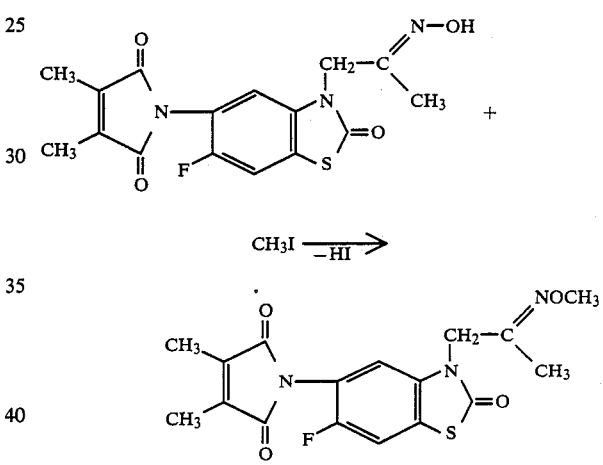

In the formula (Ia) of the starting materials employed in the process (a), the symbol X has the meaning stated above.

The compounds of the formula (Ia) fall within the scope of the present compounds of the formula (I). The compounds of the formula (Ia) can generally be prepared according to process (b) by reacting compounds of the formula (IVa)

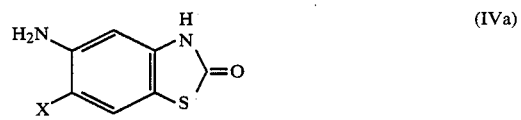

(IVa)

wherein X has the meaning stated above, with 2,3-dimethylmaleic anhydride, in an organic acid or in a solvent composed of hydrocarbons with a high boiling point, in the presence of a catalyst such as toluenesulfonic acid.

The compounds of the formula (IVa) fall within the scope of the compounds of the formula (IV), and are described in Japanese Patent Application No. 155093/1987. The compounds of the formula (IVa) may be prepared by reducing a compound of the formula:

$$\text{(VIII)}$$

[Structure: O$_2$N and X substituents on benzene ring fused with N(H)–S ring with =O]

wherein X has the meaning stated above.

The compounds of formula (VIII) are known compounds.

In the formula (III) of the starting materials employed in the process (a), the symbols $R^1$ and $M^1$ have the meanings stated above. Preferably, $R^1$ has the preferred meanings stated above, and $M^1$ represents chlorine, bromine or iodine.

The compounds of the formula (III) are known compounds. Examples of these compounds are:
Propargyl bromide;
3-bromo-propane;
3-chloro-propene;
chloromethyl methyl ether;
chloromethyl methyl sulfide;
ethyl chloroacetate;
cyclopentyl bromoacetate;
chloroacetonitrile;
1-chloro-2-propanone; and
trimethylsilylmethyl chloride.

In the formula (IV) of the starting compounds employed in the process (b), the symbols X and $R^1$ has the meanings stated above, and preferably have the preferred meanings stated above.

The compounds of the formula (IV) can generally be prepared by reducing compounds of the formula:

$$\text{(IX)}$$

[Structure: O$_2$N and X substituents on benzene ring fused with N($R^1$)–S ring with =O]

wherein X and $R^1$ have the meanings stated above.

The compounds of the formula (IX) can be prepared by reacting a compound of the formula (VIII) with a compound of the formula (III).

The compounds of the formula (Ib) employed in the process (c), and the compounds of the formula (Ic) employed in the process (d) fall within the scope of the present compounds of the formula (I).

In the formula (VII) of the starting compounds employed in the process (e), the symbols $R^4$ and $M^1$ have the meanings stated above, and preferably have the preferred meanings stated above.

The compounds of the formula (VII) are known compounds. Examples of the compound (VII) are iodomethane, iodoethane, 3-bromo-propene and propargyl bromide.

As appropriate diluents to be used in carrying out the process (a), any kind of inert organic solvents can be mentioned.

Examples of the diluents are water, nitriles such as acetonitrile, alcohols such as ethanol, acid amides such as dimethylformamide, sulfoxides such as dimethylsulfoxide, ketones such as acetone, and the like.

The process (a) may be conducted in the presence of a base. Examples of such a base are sodium carbonate, sodium hydride, potassium carbonate, potassium hydroxide, sodium hydroxide, sodium methoxide, sodium ethoxide, potassium tert-butoxide, and the like.

The reaction temperature of the process (a) may vary in a fairly wide range. In general, the reaction is carried out at a temperature of about 20° to about 150° C., preferably a temperature of about 30° to about 100° C. It is preferred to carry out the reaction under normal pressure, although a higher or lower pressure can also be used.

In the process (a), it is possible to employ about 1 to 1.2 moles of a compound (III) per mole of the compound of formula (Ia). The two starting compounds may be reacted with each other in an inert solvent in the presence of a base to obtain the desired compound of the formula (I).

As appropriate diluents to be used in carrying out the process (b), any kind of inert solvents can be mentioned; for example, the solvents similar to those exemplified for the process (a) may be mentioned. It is also possible to use, as the solvents, organic acids such as acetic acid, propionic acid, etc.

The process (b) may be carried out at temperatures of a substantially wide range. It may be carried out at a temperature, for example, of about 70° to about 280° C., preferably about 80° to about 140° C.

In the process (b), the reaction is preferably carried out under normal pressure, but it may be operated under a higher or a lower pressure.

In the process (b), it is possible to use about 1 to 1.2 moles of 2,3-dimethylmaleic anhydride per mole of the compound of the formula (IV). The reaction may be carried out in the presence of acetic acid, so that the desired compounds of the formula (I) can be produced.

The oxidation reactions in the process (c) may be carried out, for instance, by employing hydrogen peroxide or peracetic acid in acetic acid, or by employing an organic peracid, e.g. m-chloro-perbenzoic acid, in chloroform.

The process (c) may generally be conducted at a temperature of 0° to about 120° C., preferably a temperature of about 20° to about 110° C.

In the process (c), the compounds of the formula (Ib) may be reacted, for instance, with a 35% aqueous hydrogen peroxide solution in acetic acid, so that the desired compounds of the formula (Ia) can be obtained. As shown in the Examples below, when the reaction is carried out at a relatively low temperature, then a sulfinyl product may be obtained. When the reaction is performed at a higher temperature, then a sulfonyl product may be obtained.

As appropriate diluents to be used in carrying out the process (d), alcohols such as methanol and ethanol may be mentioned.

The reaction in the process (d) can be conducted at a temperature of about 30° to about 90° C. The reaction may be advantageously carried out under normal pressure, although a higher or lower pressure may also be used.

In this process (d), it is possible to employ a slightly excess amount of hydroxylamine per mole of the compound of the formula (Ic), so as to produce the desired compounds of the formula (Id).

As appropriate diluents to be used in carrying out the alkalation reaction in the process (e), the solvents similar to those exemplified for the process (a) may be mentioned. In the acylation reaction, use may be made, for instance, of ethers, benzene, toluene, etc., as solvents.

The process (e) may be carried out in the presence of a base. In the alkalation reaction, use may, for instance, be made of the bases similar to those exemplified for the process (a). In the acylation reaction, it is possible to use, for example, an organic amine such as pyridine, triethylamine, N,N-dimethylaniline or the like.

In the process (e), the alkylation reaction may be carried out under the same temperature conditions as those of the process (a). The acylation reaction may generally be conducted at a temperature of about −20° to about 60° C., preferably a temperature of about 10° to about 30° C. It is preferred to carry out such a reaction under normal pressure, although a higher or lower pressure may also be used.

In carrying out the process (e), it is possible to employ about 1 to 1.2 moles of the compounds of the formula (VII) per mole of the compound of the formula (Id), and to react the two starting materials with each other in an inert solvent in the presence of a base, so that the desired compounds of the formula (Ie) can be obtained.

The active compounds according to the invention can be used as defoliants, desiccants, agents for destroying broad-leaved plants and, especially, as weedkillers. By weeds, in the broadest sense, there are to be understood all plants which grow in locations where they are undesired. Whether the substances according to the invention act as total or selective herbicides depends essentially on the amount used.

The active compounds according to the invention can be used, for example, in connection with the following plants:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver and Centaurea.

Dicotyledon cultures of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon cultures of the genera: Oryza, Zea, Triticum, Hordium, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total combating of weeds, for example on industrial terrain and rail tracks, and on paths and squares with or without tree plantings. Equally, the compounds can be employed for combating weeds in perennial cultures, for example afforestations, decorative tree plants, orchards, vineyards, citrus groves, nut orchards, banana plantations, coffee plantations, tea plantations, rubber plantations, oil palm hopfields, and for the selective combating of weeds in annual cultures.

The active compounds can be converted into the customary formulations, such as solutions, emulsions, wettable powders, suspensions, powders, foams, pastes, granules, aerosols, natural and synthetic materials impregnated with active compound, very fine capsules in polymeric substances, coating compositions for use on seed, and formulations used with burning equipment, such as fumigating cartridges, fumigating cans and fumigating coils, as well as ULV cold mist and warm mist formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or form-forming agents. In the case of the use of water as an extender, organic solvents can, for example, also be used as auxiliary solvents.

As liquid solvents diluents or carriers, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethyl-sulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins; clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulation.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese boron, copper, cobalt, molybdenum and zinc.

The formulations in general contain from 0.1 to 95 percent by weight of active compound, preferably from 0.5 to 90 percent by weight.

The active compounds according to the invention, as such or in the form of their formulations, can also be used, for combating weeds, as mixtures with known herbicides, finished formulations or tank mixes being possible.

Mixtures with other known active compounds, such as herbicides, fungicides, insecticides, acaricides, nematicides, bird repellents, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing or scattering.

The active compounds according to the invention can be applied either before or after emergence of the plants.

They can also be incorporated into the soil before sowing. They are used, in particular, after emergence of the plants.

The amount of active compound used can vary within a substantial range. It depends essentially on the nature of the desired effect. In general, the amounts used are between 0.0001 and 3 kg of active compound per hetare of soil surface, preferably between 0.001 and 2 kg per ha.

The preparation and use of the active compounds according to the invention can be seen from the following examples.

PREPARATIVE EXAMPLES

EXAMPLE 1

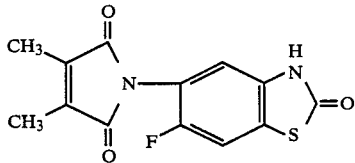

A mixture of 2,3-dimethylmaleic anhydride (13.9 g), 5-amino-6-fluoro-2-benzothiazolone (18.4 g) and Dowtherm A (an eutectic diphenyl ether/biphenyl (73.5/26.5) mixture) (200 g) was heated to a temperature of 200° to 240° C. for 10 minutes. The mixture was then admixed with p-toluenesulfonic acid (0.2 g) and heated under reflux for 15 minutes. The water, which had evolved during this reaction, was distilled off. The reaction mixture was cooled to a temperature of 40° to 60° C., admixed with n-hexane (300 ml) and stirred. The solid precipitate thus formed was separated by means of filtration, washed with n-hexane (150 ml×2), and then dissolved in tetrahydrofuran (1 liter). The resulting solution was filtered, treated with an active carbon, and then evaporated under reduced pressure to dryness. The solid thus obtained was admixed with ethanol (150 ml), heated under reflux for 5 minutes, thereafter cooled to a temperature of 10° to 15° C. for 1 hour, and then filtered. A crystalline substance thus obtained was washed with a small amount of ethanol and dried, so that the desired 5-(3,4-dimethylmaleinimido)-6-fluoro-2-benzothiazolone (21 g) was obtained. mp. 303°-305° C.

EXAMPLE 2

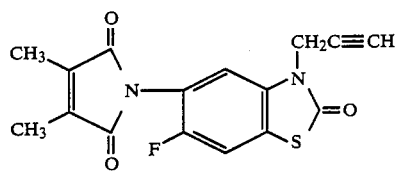

A mixture of 5-amino-6-fluoro-3-propargyl-2-benzothiazolone (2.22 g), 2,3-dimethylmaleic anhydride (1.3 g) and acetic acid (50 ml) was stirred at a temperature of 20° to 30° C., for one hour and then heated for 1 hour under reflux. The acetic acid was distilled off from the reaction mixture under reduced pressure, and the resulting residue was dissolved in ethyl acetate (100 ml), washed with 5% aqueous potassium hydroxide, water and saturated aqueous sodium chloride, in that order, dried over anhydrous sodium sulfate and then evaporated to dryness under reduced pressure.

The reaction product was purified by means of silica gel column chromatography using an eluant of toluene/tetrahydrofuran (4/1) to obtain the desired 5-(3,4-dimethylmaleinimido)-6-fluoro-3-propargyl-2-benzothiazolone (1.3 g) having a melting point in the range from 227° to 229° C.

EXAMPLE 3

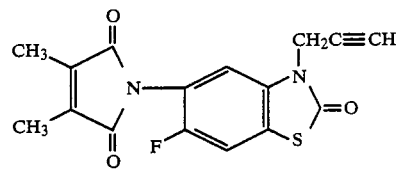

A mixture of 5-(3,4-dimethylmaleinimido)-6-fluoro-2-benzothiazolone (2.92 g), potassium carbonate (1.52 g) and acetonitrile (80 ml) was stirred at a temperature of 45° to 50° C. for 30 minutes. Thereafter, to the mixture was dropwise added propargyl bromide (1.3 g). The reaction mixture was stirred at a temperature of 70° to 80° C. for 3 hours, and then cooled to room temperature. The solvent was distilled off under reduced pressure, and the resulting residue was purified as in Example 2, so that the desired 5-(3,4-dimethylmaleinimido)-6-fluoro-3-propargyl-2-benzothiazolone (2.8 g) was obtained. mp. 227°-229° C.

EXAMPLE 4

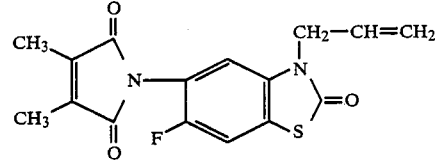

A mixture of 5-(3,4-dimethylmaleinimido)-6-fluoro-2-benzothiazolone (2.92 g), potassium carbonate (1.52 g) and acetonitrile (80 ml) was stirred at a temperature of 50° to 60° C., for 30 minutes. To the mixture there was dropwise added 3-bromopropene (1.34 g).

The reaction mixture was stirred at a temperature of 50° to 60° C., for 1 hour, and then stirred under reflux for 3 hours. Thereafter, the reaction mixture was cooled to a temperature of 10° to 20° C., and filtered. The filtrate was evaporated under reduced pressure, and the resulting residue was admixed with water (30 ml) and ethyl acetate (100 ml). The mixture thus obtained was stirred. Thereafter, the organic layer thus formed was separated out. The separated organic layer was washed with 5% aqueous potassium hydroxide and with saturated aqueous sodium chloride in that order. The organic layer was dried over anhydrous sodium sulfate, and the ethyl acetate was distilled off under reduced pressure. The resultant residue was dissolved in a minimum amount of hot ethanol, and the solution thus formed was cooled to a temperature of 5° to 10° C., overnight. Thereafter, the crystalline substance thus formed was separated by means of filtration, and dried, so that the desired 5-(3,4-dimethylmaleinimido)-6-fluoro-3-(propen-3-yl)-2-benzothiazolone (2.26 g) was obtained. mp. 159°-162° C.

EXAMPLE 5

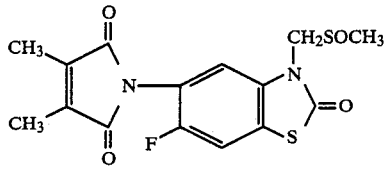

5-(3,4-imethylmaleinimido)-6-fluoro-3-methylthiomethyl-2-benzothiazolone (2 g) was dissolved in acetic acid (100 ml). To this solution was dropwise added 35% aqueous hydrogen peroxide (0.65 g) at a temperature of 10° to 20° C. The reaction mixture was stirred at a temperature of 10° to 20° C., for 1 hour, and then stirred at a temperature of 20° to 30° C., for 8 hours. The reaction mixture was admixed with aqueous ferrous chloride to decompose the excess hydrogen peroxide. Thereafter, the acetic acid was distilled off. The residue thus obtained was dissolved in ethyl acetate (80 ml). The resulting solution was washed with saturated aqueous sodium hydrogen carbonate, and then with saturated aqueous sodium chloride, and dried over anhydrous sodium sulfate. Thereafter, active carbon was added to the mixture, which was then filtered. The filtrate was evaporated to dryness under reduced pressure. The resultant residue was recrystallized from ethanol, so that the desired 5-(3,4-dimethylmaleinimido)-6-fluoro-3-methylsulfinylmethyl-2-benzothiazolone (1 g) was obtained. mp. 250°-251.5° C.

EXAMPLE 6

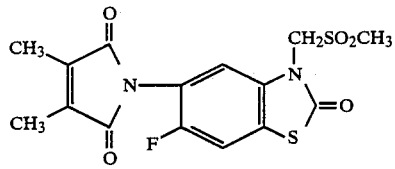

5-(3,4-Dimethylmaleinimido)-6-fluoro-3-methylthiomethyl-2-benzothiazolone (0.704 g) was dissolved in acetic acid (50 ml). To this solution was added 35% aqueous hydrogen peroxide (0.43 g) at a temperature of 20° to 30° C. The reaction mixture was stirred at a temperature of 30° to 40° C., for 1 hour, and then stirred under reflux for 5 hours. A small amount of aqueous ferrous chloride was added in order to decompose the excess hydrogen peroxide. The reaction mixture was then evaporated under reduced pressure to dryness. The residue thus obtained was admixed with ethyl acetate (80 ml) and active carbon (0.4 g), and the reaction mixture was stirred and then filtered. The filtrate was washed with saturated aqueous sodium hydrogen carbonate and then with saturated aqueous sodium chloride, dried over anhydrous sodium sulfate, and evaporated to dryness under reduced pressure. The resulting residue was recrystallized from ethanol, so that the desired 5-(3,4-dimethylmaleinimido)-6-fluoro-3-methylsulfonylmethyl-2-benzothiazolone (0.7 g) was obtained. mp. 282°-283.5° C.

EXAMPLE 7

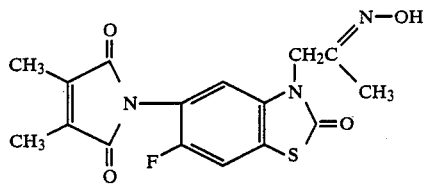

A mixture of 5-(3,4-dimethylmaleinimido)-6-fluoro-2-oxopropyl)-2-benzothiazolone (5.5 g), hydroxylamine hydrochloride (2 g) and methanol (220 ml) was heated under reflux for 2 hours. The methanol was distilled off under reduced pressure, and the residue was admixed with water (50 ml) and ethyl acetate (250 ml). The mixture thus formed was stirred, and then an organic layer was separated therefrom. The separated organic layer was washed with water and with saturated aqueous sodium chloride in that order, dried over anhydrous sodium sulfate, and evaporated to dryness under reduced pressure. The resultant residue was recrystallized from methanol, so that the desired 5-(3,4-dimethylmaleinimido)-6-fluoro-3-(2-hydroxyiminopropyl)-2-benzothiazolone (2.3 g) was obtained. mp. 252°-253° C.

EXAMPLE 8

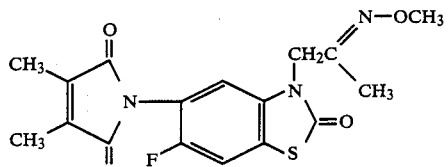

A mixture of 5-(3,4-dimethylmaleinimido)-6-fluoro-3-(2-hydroxyiminopropyl)-2-benzothiazolone (0.92 g), potassium carbonate (0.36 g) and methanol (80 ml) was stirred at a temperature of 40° to 50° C. for 20 minutes, and iodomethane (0.43 g) was dropwise added to this mixture. The reaction mixture was stirred under reflux for 3 hours, and subjected to a distillation operation to remove the low boiling substances therefrom. The residue was admixed with water (10 ml) and ethyl acetate (60 ml), and the resultant mixture was stirred. An organic layer thus formed was separated out. The separated organic layer was washed with water and with saturated aqueous sodium chloride in this order, dried over anhydrous sodium sulfate, and evaporated to dryness under reduced pressure. The resultant residue was purified by means of silica gel column chromatography employing a toluene/tetrahydrofuran (5/1) mixture as an eluant, so that the desired 5-(3,4-dimethylmaleimido)-6-fluoro-3-(2-methoxyiminopropyl)-2-benzothiazolone (0.27 g) was obtained. mp. 282°–283.5° C.

EXAMPLE 9

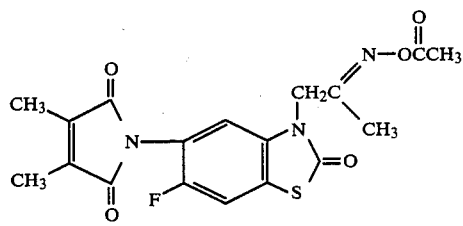

5-(3,4-Dimethylmaleinimido)-6-fluoro-3-(2-hydroxyiminopropyl)-2-benzothiazolone (0.91 g) was dissolved in tetrahydrofuran (30 ml), and the mixture thus formed was admixed with triethylamine (0.26 g) and cooled to a temperature of −10° to 0° C. To the mixture was dropwise added a solution of acetyl chloride (0.2 g) in tetrahydrofuran (10 ml) at a temperature of −10° to 0° C. Then the reaction mixture was stirred at a temperature of 0° to 10° C. for 2 hours, and thereafter allowed to stand overnight at a temperature of 20° to 30° C. The tetrahydrofuran was distilled off under reduced pressure, and the residue was admixed with water (10 ml) and ethyl acetate (30 ml). The resultant mixture was stirred, and an organic layer thus formed was separated out. The separated organic layer was washed with saturated aqueous sodium hydrogen carbonate and with saturated aqueous sodium chloride in that order, and dried over anhydrous sodium sulfate. The solvent was distilled off under reduced pressure, so that the desired 3-(2-acetoxyiminopropyl)-5-(3,4-dimethylmaleinimido)-6-fluoro-2-benzothiazolone (0.8 g) was obtained as a viscous liquid.

In the same way as described in Examples 1 to 9, various compounds (I) according to the invention were prepared. These compounds are shown, together with the compounds of Examples 1 to 9, in Table 1.

TABLE 1

| Compound No. | X | R$^1$ | mp. (°C.) |
|---|---|---|---|
| 1 | H | H | 300–305 |
| 2 | H | —C$_3$H$_7$ | |
| 3 | H | —CH$_2$CH=CH$_2$ | |
| 4 | H | —CH$_2$C(Cl)=CH$_2$ | |
| 5 | H | —CH$_2$C≡CH | 226–267 |
| 6 | H | —CH$_2$C(O)—CH$_3$ | |
| 7 | F | H | 303–305 |
| 8 | F | —CH$_3$ | 255–260 |
| 9 | F | —C$_2$H$_5$ | 207–210 |
| 10 | F | —C$_3$H$_7$-iso | 163–166 |
| 11 | F | —C$_3$H$_7$ | 172–173 |
| 12 | F | —C$_4$H$_9$-n | |
| 13 | F | —C$_4$H$_9$-sec | |
| 14 | F | —CH$_2$CH$_2$Cl | |
| 15 | F | —CH$_2$CH$_2$CH$_2$Cl | |
| 16 | F | —CH$_2$CH=CH$_2$ | 159–162 |
| 17 | F | —CH$_2$C(Cl)=CH$_2$ | 189–192 |
| 18 | F | —CH$_2$CH=CHCl | |
| 19 | F | —CH$_2$C(Cl)=CHCl | |
| 20 | F | —CH$_2$C(CH$_3$)=CH$_2$ | 177–179 |
| 21 | F | —CH$_2$C≡CH | 227–229 |
| 22 | F | —CH$_2$C≡CCH$_3$ | |
| 23 | F | —CH(CH$_3$)C≡CH | 191–199 |
| 24 | F | —CH$_2$C≡N | 214–218 |
| 25 | F | —CH(CH$_3$)—C≡N | 188–191 |
| 26 | F | —CH$_2$C(O)NH$_2$ | |
| 27 | F | —CH$_2$C(S)NH$_2$ | |
| 28 | F | —CH$_2$OCH$_3$ | 202–207 |
| 29 | F | —CH$_2$OC$_2$H$_5$ | |
| 30 | F | —CH$_2$OC$_3$H$_7$ | |
| 31 | F | —CH$_2$SCH$_3$ | 207–209 |
| 32 | F | —CH$_2$S(O)CH$_3$ | 250–251.5 |
| 33 | F | —CH$_2$S(O)$_2$CH$_3$ | 282–283.5 |
| 34 | F | —CH$_2$SC$_2$H$_5$ | |
| 35 | F | —CH$_2$S(O)C$_2$H$_5$ | |
| 36 | F | —CH$_2$S(O)$_2$C$_2$H$_5$ | |
| 37 | F | —CH$_2$CH$_2$SC$_2$H$_5$ | |
| 38 | F | —CH$_2$CH$_2$S(O)C$_2$H$_5$ | |
| 39 | F | —CH$_2$CH$_2$S(O)$_2$C$_2$H$_5$ | |
| 40 | F | —CH$_2$S—C$_6$H$_5$ | |

TABLE 1-continued

| Compound No. | X | R¹ | mp. (°C.) |
|---|---|---|---|
| 41 | F | —CH₂S—⟨C₆H₄⟩—Cl | |
| 42 | F | —CH₂—⟨C₆H₅⟩ | 236–237 |
| 43 | F | —CH₂—⟨C₆H₄⟩—F (ortho) | |
| 44 | F | —CH₂—⟨C₆H₄⟩—Cl | |
| 45 | F | —CH₂—⟨C₆H₄⟩—OCH₃ | |
| 46 | F | —CH₂C(O)—CH₃ | 252–253 |
| 47 | F | —CH(CH₃)—C(O)—CH₃ | |
| 48 | F | —CH₂C(O)—C₂H₅ | |
| 49 | F | —CH(CH₃)—C(O)—C₂H₅ | |
| 50 | F | —CH(C₂H₅)—C(O)—C₃H₇ | |
| 51 | F | —CH₂—C(O)—cyclopropyl | |
| 52 | F | —CH₂—C(O)—⟨C₆H₅⟩ | |
| 53 | F | —CH₂—C(O)—⟨C₆H₄⟩—Cl | |
| 54 | F | —CH₂C(=N—OH)CH₃ | 252–253 |
| 55 | F | —CH₂C(=N—OCH₃)CH₃ | 194–196 |
| 56 | F | —CH₂C(=N—OC₂H₅)CH₃ | |
| 57 | F | —CH₂C(=N—OCH₂CH=CH₂)CH₃ | |
| 58 | F | —CH₂C(=N—OCH₂C≡CH)CH₃ | |
| 59 | F | —CH₂C(=N—O—CH₂—⟨C₆H₅⟩)CH₃ | |
| 60 | F | —CH₂C(=N—OC(O)CH₃)CH₃ | viscous liquid |
| 61 | F | —CH₂C(=N—OSO₂CH₃)CH₃ | |
| 62 | F | —CH₂Si(CH₃)₃ | |
| 63 | F | —CH₂COOC₂H₅ | 154–157 |
| 64 | F | —CH₂COO—cyclopentyl | |
| 65 | F | —CH(CH₃)COOC₂H₅ | 131–132 |

Biotest Examples

Known compound employed for comparison:

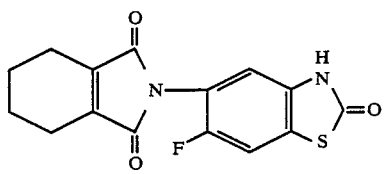

(The comparative compound is shown in Japanese Patent Laid-open No. 155276/1987.)

EXAMPLE 10

Pre-emergence soil treatment test against upland weeds

Preparation of an active compound formulation

Carrier: 5 parts by weight of acetone
Emulsifier: 1 part by weight of benzyloxy polyglycol ether A formulation of an active compound was obtained as an emulsifiable concentrate by mixing 1 part by weight of the active compound with the above-mentioned amounts of the carrier and the emulsifying agent. A predetermined amount of the formulation was diluted with water.

Testing method

In a greenhouse, soybean seeds were sown in 500 cm² pots filled with upland farm soil, and soil containing seeds of barnyard grass (*Echinochloa crus-galli*), livid amaranth (*Amaranthus lividus* L.) and goosefoot (*Chenopodium album* L.) was put over the soil in the pots in a depth of 1 cm.

One day after the sowing, a test chemical in a predetermined concentration, prepared hereinabove, was uniformly sprayed over the surface layer of the soil in each of the test pots.

Four weeks after the spraying, the herbicidal effect and the phytotoxicity to crops were evaluated and rated on the scale of 0 to 5 as follows:

Herbicidal effect (evaluated by a weed killing ratio based on a non-treated lot):
5: at least 95% (withered)
4: at least 80% but less than 95%
3: at least 50% but less than 80%
2: at least 30% but less than 50%
1: at least 10% but less than 30%
0: less than 10% (no effect)

Phytotoxicity to crop (evaluated based on a non-treated lot):
5: at least 90% (fatal injury)
4: at least 50% but less than 90%
3: at least 30% but less than 50%
2: at least 10% but less than 30%
1: more than 0 but less than 10%
0: 0% (no phytotoxicity)

The test results are shown in Table 2.

TABLE 2

| Active compound No. | Amount of active compound (kg/ha) | Herbicidal effect on weeds | | | Phytotoxic effect on soy bean plants |
|---|---|---|---|---|---|
| | | Barnyard grass | Livid amaranth | Goose foot | |
| 17 | 0.25 | 4 | 5 | 5 | 0 |
|  | 0.125 | 3 | 5 | 5 | 0 |
| 21 | 0.25 | 5 | 5 | 5 | 0 |
|  | 0.125 | 4 | 5 | 5 | 0 |
| 46 | 0.25 | 4 | 5 | 5 | 1 |
|  | 0.125 | 3 | 5 | 5 | 0 |
| (Control compound) | | | | | |
| E-1 | 0.25 | 0 | 4 | 3 | 0 |
|  | 0.125 | 0 | 3 | 1 | 0 |

EXAMPLE 11

Herbicidal test by foliage application on upland weeds

In a greenhouse, maize seeds were sown in 500 cm² pots filled with upland farm soil, and soil containing seeds of Polygonum (*Polygonum blumei* Meisn.), livid amaranth (*Amaranthus lividus* L.) and goosefoot (*Chenopodium album* L.) was put over the soil in the pots in a depth of 1 cm.

After sowing, the plants were grown for 14 days and a test chemical in a predetermined concentration, prepared as in Example 10, was uniformly sprayed over the test plants in each of the test pots.

Four weeks after the spraying, the herbicidal effect and the phytotoxicity to crops were examined on the same standards as in Example 10. The results are shown in Table 3.

TABLE 3

| Active compound No. | Amount of active compound (kg/ha) | Herbicidal effect on weeds | | | Phytotoxicity on corn plants |
|---|---|---|---|---|---|
| | | Polygonum | Livid amaranth | Goose foot | |
| 17 | 0.125 | 5 | 5 | 5 | 1 |
|  | 0.06 | 4 | 5 | 5 | 0 |
| 21 | 0.125 | 5 | 5 | 5 | 1 |
|  | 0.06 | 4 | 5 | 5 | 0 |
| 32 | 0.125 | 5 | 5 | 5 | 1 |
|  | 0.06 | 5 | 5 | 5 | 0 |
| (Control compound) | | | | | |
| E-1 | 0.125 | 3 | 3 | 2 | 1 |
|  | 0.06 | 1 | 2 | 1 | 0 |

It will be appreciated that the instant specification and claims are set forth by way of illustration and not limitation, and that various modifications and changes may be made without departing from the spirit and scope of the present invention.

I claim:

1. A benzothiazoline of the formula

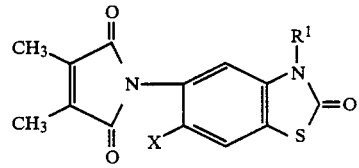

(I)

wherein
X represents hydrogen or halogen,
$R^1$ represents hydrogen, alkyl with 1 to 5 carbon atoms optionally substituted with halogen, alkenyl with 3 to 5 carbon atoms optionally substituted with halogen, alkynyl with 3 to 4 carbon atoms optionally substituted with halogen, alkoxyalkyl with 2 to 5 carbon atoms in total, alkylthioalkyl with 2 to 5 carbon atoms in total, alkylsulfinylalkyl with 2 to 5 carbon atoms in total, alkylsulfonylalkyl with 2 to 5 carbon atoms in total; arylthioalkyl with 7 to 8 carbon atoms in total and optionally substituted with halogen, cyanoalkyl having an alkyl moiety with 1 to 2 carbon atoms, carbamoylmethyl, thiocarbamoylmethy, alkoxycarbonylalkyl with 3 to 8 carbon atoms in total, cycloalkoxycarbonylmethyl having a cycloalkyl moiety with 3 to 7 carbon atoms, thialkylsilylmethyl with 4 to 10 carbon atoms in total, or a radical of the formula $$-\overset{R^2}{\underset{|}{CH}}-\overset{O}{\underset{\|}{C}}-R^3, \quad -\overset{R^2}{\underset{|}{CH}}-C\overset{N-OR^4}{\underset{R^3}{\diagdown}} \quad \text{or} \quad -\overset{R^2}{\underset{|}{CH}}-C\overset{NNR^5R^6}{\underset{R^3}{\diagdown}}$$

in which
$R^2$ represents hydrogen or alkyl with 1 to 3 carbon atoms,
$R^3$ represents alkyl with 1 to 4 carbon atoms, cycloalkyl with 3 to 6 carbon atoms, or phenyl optionally substituted with halogen,
$R^4$ represents hydrogen, alkyl with 1 to 4 carbon atoms, alkenyl with 3 to 4 carbon atoms, alkynyl with 3 to 4 carbon atoms, aralkyl with 7 to 9 carbon atoms in total, alkylcarbonyl having an alkyl moiety with 1 to 4 carbon atoms, or alkanesulfonyl with 1 to 4 carbon atoms, and
$R^5$ and $R^6$ each represent hydrogen or alkyl with 1 to 4 carbon atoms.

2. A compound according to claim 1, wherein
X represents hydrogen or fluorine,
$R^1$ represents hydrogen, alkyl with 1 to 4 carbon atoms optionally substituted with chlorine, alkenyl with 3 to 4 carbon atoms optionally substituted with chlorine, alkynyl with 3 to 4 carbon atoms optionally substituted with chlorine, alkoxyalkyl with 2 to 4 carbon atoms in total; alkylthioalkyl with 2 to 3 carbon atoms in total, alkylsulfinylalkyl with 2 to 4 carbon atoms in total, alkylsulfonylalkyl with 2 to 4 carbon atoms in total, phenylthiomethyl optionally substituted with chlorine, cyanomethyl, carbamoylmethyl, thiocarbamoylmethyl; alkoxycarbonylalkyl with 3 to 6 carbon atoms in total, cycloalkoxycarbonylmethyl having a cycloalkyl moiety with 3 to 6 carbon atoms, trimethylsilylmethyl, or a radical of the formula $$-\overset{R^2}{\underset{|}{CH}}-\overset{O}{\underset{\|}{C}}-R^3, \quad -\overset{R^2}{\underset{|}{CH}}-C\overset{N-OR^4}{\underset{R^3}{\diagdown}} \quad \text{or} \quad -\overset{R^2}{\underset{|}{CH}}-C\overset{NNR^5R^6}{\underset{R^3}{\diagdown}}$$

in which
$R^2$ represents hydrogen, methyl or ethyl,
$R^3$ represents alkyl with 1 to 3 carbon atoms, cycloalkyl with 3 to 5 carbon atoms, or phenyl optionally substituted with fluorine and/or with chlorine,
$R^4$ represents hydrogen, alkyl with 1 to 3 carbon atoms, allyl, propargyl, benzyl; alkylcarbonyl having an alkyl moiety with 1 to 3 carbon atoms, or alkanesulfonyl with 1 to 2 carbon atoms; and $R^5$ and $R^6$ each represent hydrogen or alkyl with 1 to 2 carbon atoms.

3. A compound according to claim 1, wherein
X represents fluorine,
$R^1$ represents hydrogen, alkyl with 1 to 3 carbon atoms optionally substituted with chlorine, allyl optionally substituted with chlorine, propargyl, alkoxymethyl having an alkoxy moiety with 1 to 3 carbon atoms, alkylthiomethyl having an alkylmercapto moiety with 1 to 2 carbon atoms, alkylsulfinylmethyl having an alkylsulfinyl moiety with 1 to 2 carbon atoms, alkylsulfonylmethyl having an alkylsulfonyl moiety with 1 to 2 carbon atoms, cyanomethyl, or a radical of the formula $$-\overset{R^2}{\underset{|}{CH}}-\overset{O}{\underset{\|}{C}}-R^3$$

in which
$R^2$ represents hydrogen or methyl, and
$R^3$ represents methyl or ethyl.

4. A compound according to claim 1 wherein such compound is 5-(3,4-dimethylmaleinimido)-6-fluoro-3-propargyl-2-benzothiazolone of the formula 5. A compound according to claim 1 wherein such compound is 3-allyl-5-(3,4-dimethylmaleinimido)-6-fluoro-2-benzothiazolone of the formula 6. A compound according to claim 1 wherein such compound is 5-(3,4-dimethylmaleinimido)-6-fluoro-3-propyl-2-benzothiazolone of the formula 7. A compound according to claim 1 wherein such compound is 3-cyanomethyl-5-(3,4-dimethylmaleinimido)-6-fluoro-2-benzothiazolone of the formula

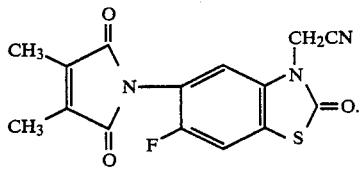

8. A compound according to claim 1 wherein such compound is 5-(3,4-dimethylmaleinimido)-6-fluoro-3-methylthiomethyl-2-benzothiazolone of the formula

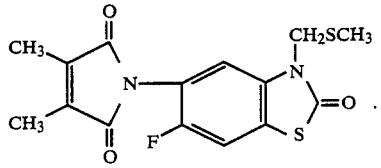

9. A compound according to claim 1 wherein such compound is 5-(3,4-dimethylmaleinimido)-6-fluoro-3-methylsulfinylmethyl-2-benzothiazolone of the formula

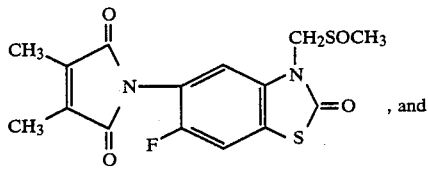

10. A compound according to claim 1 wherein such compound is 5-(3,4-dimethylmaleinimido)-6-fluoro-3-methylsulfonylmethyl-2-benzothiazolone of the formula

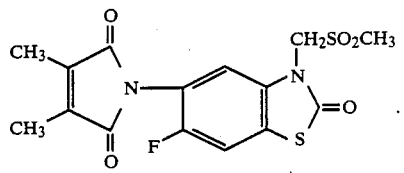

11. A herbicidal composition comprising a herbicidally effective amount of a compound according to claim 1 and a diluent.

12. A method of combating unwanted vegetation which comprises applying to such vegetation or to a locus from which it is desired to exclude such vegetation a herbicidally effective amount of a compound according to claim 1.

13. The method according to claim 12, wherein such compound is
5-(3,4-dimethylmaleinimido)-6-fluoro-3-propargyl-2-benzothiazolone,
3-allyl-5-(3,4-dimethylmaleinimido)-6-fluoro-2-benzothiazolone,
5-(3,4-dimethylmaleinimido)-6-fluoro-3-propyl-2-benzothiazolone,
3-cyanomethyl-5-(3,4-dimethylmaleinimido)-6-fluoro-2-benzothiazolone,
5-(3,4-dimethylmaleinimido)-6-fluoro-3-methylthiomethyl-2-benzothiazolone,
5-(3,4-dimethylmaleinimido)-6-fluoro-3-methylsulfinylmethyl-1-benzothiazolone and
5-(3,4-dimethylmaleinimido)-6-fluoro-3-methylsulfonylmethyl-2-benzothiazolone.

* * * * *

UNITED STATES PATENT AND TRADEMARK OFFICE
CERTIFICATE OF CORRECTION

PATENT NO. : 4,971,619

DATED : November 20, 1990

INVENTOR(S) : Kume et al.

It is certified that error appears in the above-identified patent and that said Letters Patent is hereby corrected as shown below:

Title Page  [75] Inventors: After " Miyauchi " delete " , " and insert -- ; Katsuhiko Shibuya, --

Title Page  [30] Foreign Application Priority Data:  After " 63-266663 " insert
-- Jun. 15, 1987 [JP] Japan ... 62-155093
Sep. 17, 1987 [JP] Japan ... 62-231063
Oct. 15, 1987 [JP] Japan ... 62-258462 --

Col. 22, line 33  Delete " $CH\equiv$ " and substitute -- $C\equiv$ --

Col. 24, line 33  Delete " -1- " and substitute -- -2- --

Signed and Sealed this

Third Day of November, 1992

*Attest:*

DOUGLAS B. COMER

*Attesting Officer*   *Acting Commissioner of Patents and Trademarks*